US007935667B2

(12) United States Patent
Tichy et al.

(10) Patent No.: US 7,935,667 B2
(45) Date of Patent: *May 3, 2011

(54) AQUEOUS DISINFECTANTS AND STERILANTS INCLUDING COLLOIDAL TRANSITION METALS

(75) Inventors: Daryl J. Tichy, Orem, UT (US); Brian G. Larson, Orem, UT (US)

(73) Assignee: Solutions BioMed, LLC, Orem, UT (US)

( * ) Notice: Subject to any disclaimer, the term of this patent is extended or adjusted under 35 U.S.C. 154(b) by 248 days.

This patent is subject to a terminal disclaimer.

(21) Appl. No.: 11/891,316

(22) Filed: Aug. 8, 2007

(65) Prior Publication Data

US 2008/0233005 A1 Sep. 25, 2008

Related U.S. Application Data

(63) Continuation of application No. 11/361,665, filed on Feb. 24, 2006, now Pat. No. 7,351,684.

(60) Provisional application No. 60/656,723, filed on Feb. 25, 2005.

(51) Int. Cl.
*C11D 7/18* (2006.01)
*C11D 3/48* (2006.01)

(52) U.S. Cl. ........ 510/372; 510/161; 510/199; 510/235; 510/238; 510/302; 510/309; 510/319; 510/362; 510/370; 510/367; 510/375; 510/382

(58) Field of Classification Search .................. 510/161, 510/199, 235, 238, 302, 309, 319, 362, 370, 510/372, 367, 375, 382
See application file for complete search history.

(56) References Cited

U.S. PATENT DOCUMENTS

| | | |
|---|---|---|
| 716,077 A | 12/1902 | Morrin |
| 734,467 A | 7/1903 | Martien |
| 2,103,999 A | 12/1937 | Muller et al. |
| 2,304,104 A | 12/1938 | Klabunde et al. |
| 4,021,338 A | 5/1977 | Harkin |
| 4,297,298 A | 10/1981 | Crommelynch et al. |
| 4,311,598 A | 1/1982 | Verachtert |
| 4,321,255 A | 3/1982 | Boden |
| 4,414,127 A | 11/1983 | Fu |
| 4,655,975 A | 4/1987 | Snoble |
| 4,751,119 A | 6/1988 | Yukawa |
| 4,826,658 A | 5/1989 | Kay |
| 4,915,955 A | 4/1990 | Gomori |
| 5,349,083 A | 9/1994 | Brougham et al. |
| 5,357,636 A | 10/1994 | Dresdner et al. |
| 5,368,867 A | 11/1994 | Da Silva et al. |
| 5,419,908 A | 5/1995 | Richter et al. |
| 5,437,858 A | 8/1995 | Hungerbach et al. |
| 5,494,644 A | 2/1996 | Thomas et al. |
| 5,508,046 A | 4/1996 | Cosentino et al. |
| 5,563,132 A | 10/1996 | Bodaness |
| 5,709,870 A | 1/1998 | Yoshimura et al. |
| 5,824,267 A | 10/1998 | Kawasumi et al. |
| 5,875,889 A | 3/1999 | Albisetti |
| 5,945,032 A | 8/1999 | Breitenbach et al. |
| 5,951,993 A | 9/1999 | Scholz et al. |
| 5,977,403 A | 11/1999 | Byers |
| 5,997,585 A | 12/1999 | Scialla et al. |
| 6,021,892 A | 2/2000 | Baudin |
| 6,027,469 A | 2/2000 | Johnson |
| 6,114,298 A | 9/2000 | Petri et al. |
| 6,197,814 B1 | 3/2001 | Arata |
| 6,200,946 B1 | 3/2001 | Blum et al. |
| 6,218,351 B1 | 4/2001 | Busch et al. |
| 6,231,848 B1 | 5/2001 | Breitenbach et al. |
| 6,242,009 B1 | 6/2001 | Batarseh et al. |
| 6,257,253 B1 | 7/2001 | Lentsch et al. |
| 6,277,414 B1 | 8/2001 | Elhaik et al. |
| 6,293,433 B1 | 9/2001 | Joulia |
| 6,302,968 B1 | 10/2001 | Baum et al. |
| 6,306,812 B1 | 10/2001 | Perkins et al. |
| 6,368,611 B1 | 4/2002 | Whitbourne et al. |
| 6,379,712 B1 | 4/2002 | Yan et al. |
| 6,436,342 B1 | 8/2002 | Petri et al. |
| 6,540,791 B1 | 4/2003 | Dias |
| 6,569,353 B1 | 5/2003 | Giletto et al. |
| 6,583,176 B2 | 6/2003 | Arata |
| 6,630,172 B2 | 10/2003 | Batarseh |
| 6,660,289 B1 | 12/2003 | Wilmotte et al. |
| 6,743,348 B2 | 6/2004 | Holladay et al. |
| 6,797,302 B1 * | 9/2004 | Ben Yehuda et al. ......... 426/335 |
| 6,827,766 B2 | 12/2004 | Carnes et al. |
| 6,866,145 B2 | 3/2005 | Richards et al. |
| 6,939,564 B2 | 9/2005 | Ranger et al. |
| 6,939,566 B2 | 9/2005 | Batarseh et al. |
| 6,959,807 B2 | 11/2005 | Sharon et al. |

(Continued)

FOREIGN PATENT DOCUMENTS

GB 2189394 10/1987

(Continued)

OTHER PUBLICATIONS

The interaction of silver ions and hydrogen peroxide in the inactivation of *E coli*; a preliminary evaluation of a new long lasitng residual drinking water disinfectant; Water Science and Technology vol. 31 No. 5-6 pp. 123-129 (1995).

(Continued)

*Primary Examiner* — Charles I Boyer
(74) *Attorney, Agent, or Firm* — Thorpe North & Western LLP

(57) ABSTRACT

The present invention is drawn to disinfectant or sterilant compositions, which are human safe, e.g., food grade or food safe. In one embodiment, an aqueous disinfectant or sterilant composition can comprise an aqueous vehicle, including water, from 0.001 wt % to 50 wt % of a peracid, and from 0.001 wt % to 25 wt % of a peroxide. Additionally, from 0.001 ppm to 50,000 ppm by weight of a transition metal based on the aqueous vehicle content can also be present. The composition can be formulated to include only food-grade ingredients. Alternatively or additionally, the transition metal can be in the form of a colloidal transition metal.

78 Claims, No Drawings

U.S. PATENT DOCUMENTS

| | | | |
|---|---|---|---|
| 6,962,714 | B2 | 11/2005 | Hei et al. |
| 7,033,511 | B2 * | 4/2006 | Zawada et al. ............... 210/764 |
| 7,083,043 | B2 | 8/2006 | Sharon |
| 2002/0137648 | A1 | 9/2002 | Sharma et al. |
| 2003/0008797 | A1 | 1/2003 | Hage et al. |
| 2003/0099717 | A1 | 5/2003 | Cabrera |
| 2003/0235623 | A1 * | 12/2003 | Van Oosterom ............. 424/616 |
| 2004/0026535 | A1 | 2/2004 | Conway et al. |
| 2004/0067159 | A1 | 4/2004 | Carnes et al. |
| 2004/0170742 | A1 * | 9/2004 | Ben Yehuda et al. ......... 426/615 |
| 2004/0234569 | A1 | 11/2004 | Nakada et al. |
| 2005/0013836 | A1 | 1/2005 | Raad |
| 2005/0173281 | A1 | 8/2005 | Goodall et al. |
| 2005/0194357 | A1 * | 9/2005 | Liu et al. ........................ 216/88 |
| 2005/0256017 | A1 | 11/2005 | Dykstra |
| 2005/0256200 | A1 | 11/2005 | Burkhart et al. |
| 2006/0035808 | A1 | 2/2006 | Ahmed et al. |
| 2006/0122082 | A1 | 6/2006 | Paul |
| 2006/0182813 | A1 | 8/2006 | Holladay |
| 2006/0198798 | A1 | 9/2006 | Tichy et al. |
| 2006/0198876 | A1 | 9/2006 | Tichy et al. |
| 2006/0199752 | A1 | 9/2006 | Tichy et al. |
| 2006/0240381 | A1 * | 10/2006 | Rizoiu et al. .................... 433/80 |
| 2006/0263239 | A1 | 11/2006 | Tichy et al. |
| 2007/0048175 | A1 | 3/2007 | Tichy et al. |
| 2007/0053850 | A1 | 3/2007 | Tichy et al. |
| 2007/0059202 | A1 | 3/2007 | Tichy et al. |
| 2007/0059255 | A1 | 3/2007 | Tichy et al. |
| 2007/0254044 | A1 | 11/2007 | Karandikar et al. |
| 2008/0000931 | A1 | 1/2008 | Tichy et al. |

FOREIGN PATENT DOCUMENTS

| | | |
|---|---|---|
| WO | WO 03/080231 | 10/2003 |
| WO | WO 2005/000324 | 1/2005 |
| WO | 2006/079109 | 7/2006 |

OTHER PUBLICATIONS

N. Surdeau et al. Sensitivity of bacterial biofilms and planktonic cells to a new antimicrobial agent, Oxsil 320N, Journal of Hospital Infection, 2006 62 487-493, www.sciencedirect.com.

Brady, Michael J. et al. "Persistent silver disinfectant for the environmental control of pathogenic bacteria," Am. J. Infect. Control, Aug. 2004, pp. 208-214, vol. 31 (4).

Brentano, Loreno et al., "Antibacterial efficacy of a colloidal silver complex," Surg. Forum, 1966, pp. 76-78, vol. 12.

Phillips, Charles R., et al., "Chemical Disinfectant," Annual Review of Microbiology, Oct. 1958, pp. 525-550, vol. 12.

Monarca, S. et al, "Decontamination of dental unit waterlines using disinfectants and filters," Abstract Only, Minerva Stomatol., Oct. 2002, vol. 10.

Yin, Huiyong, "Analysis of Diacyl Peroxides by Ag+Coordination Ionspray Tandem Mass Spectrometry: Free Radical Pathways of Complex Decomposition," J. Am. Soc. Mass Spectrum, Apr. 2001, pp. 449-455, vol. 12 (4).

Schuster, A. et al., "Persistent silver disinfectant for the enviromental myth and reality," Am. J. Infect. Control, Jun. 2003, pp. 309-311, vol. 32.

http://web.archive.org/web/20060217191603/http://sanosilbiotech.com/start_food.html, Virosil F&B, "Swift Virucidal with Swiss Precision," Feb. 17, 2006, 5 pages.

* cited by examiner

AQUEOUS DISINFECTANTS AND STERILANTS INCLUDING COLLOIDAL TRANSITION METALS

This application is a continuation of U.S. patent application Ser. No. 11/361,665, filed Feb. 24, 2006, which claims the benefit of U.S. Provisional Application Ser. No. 60/656,723, filed on Feb. 25, 2005, each of which is incorporated herein by reference in its entirety.

FIELD OF THE INVENTION

The present invention is drawn to consumer safe compositions and methods for their use, including for hard surface cleaning. The compositions are effective as disinfectants or even sterilants.

BACKGROUND OF THE INVENTION

Disinfectant and sterilants, such as hard surface disinfectants and sterilants, are widely used in both domestic and professional settings. Generally, though both sterilants and disinfectants are used for the same purpose, i.e. to kill bacteria and/or viruses, etc., a sterilant composition exhibits a greater kill level compared to a disinfectant. This being stated, most applications require only disinfectant levels bacteria/virus reduction, though other applications benefit considerably from the use of sterilants. For example, in the medical/dental industries, hard surfaces such as floors, walls, countertops, medical/dental instruments and equipment, etc., need to be clean or even sterilized for safe patient care.

Exemplary of a commonly used hard surface cleaner is Lysol® disinfectant. Though Lysol® is effective for many applications; Lysol® is not as effective at reducing levels of bacteria as commercially available glutaraldehyde aqueous solutions. Glutaraldehyde aqueous solutions are widely used as disinfectants (and often as sterilants), and are commonly available in 1 wt % and 2 wt % solutions, particularly in medical and dental settings. Glutaraldehyde solutions are typically used for more delicate medical/dental instruments that would otherwise be susceptible to damage by other sterilization methods, e.g., autoclaving. However, glutaraldehyde is also a powerful irritant and respiratory sensitizer. In fact, there have been reports of sensitization of individuals due to the fumes, which have lead to respiratory problems, headaches, lethargy, discoloring of the skin, etc. Because of these issues related to glutaraldehyde fumes, air quality must often be monitored, or appropriate air ventilation must be present. As a result, though glutaraldehyde solutions are relatively effective disinfectants, and even sterilants, it would be desirable to provide compositions that can exhibit even more effective bacteria kill levels, and at the same time be safer for the individuals using the disinfectant/sterilant.

SUMMARY OF THE INVENTION

It has been recognized that it would be desirable to provide liquid solution and dispersion disinfectants that are effective for cleaning surfaces, particularly hard surfaces. In accordance with this, an aqueous disinfectant or sterilant composition can comprise an aqueous vehicle, including water, from 0.001 wt % to 50 wt % of a peracid, and from 0.001 wt % to 25 wt % of a peroxide. Additionally, from 0.001 ppm to 50,000 ppm by weight of a colloidal transition metal based on the aqueous vehicle content can also be present.

In another embodiment, a method for cleaning hard surfaces includes contacting the hard surface with a disinfectant comprising an aqueous vehicle, including water, from 0.001 wt % to 50 wt % of a peracid, and from 0.001 wt % to 25 wt % of a peroxide. Additionally, from 0.001 ppm to 50,000 ppm by weight of a colloidal transition metal based on the aqueous vehicle content can also be present.

Additional features and advantages of the invention will be apparent from the detailed description that follows, which illustrates, by way of example, features of the invention.

DETAILED DESCRIPTION OF THE PREFERRED EMBODIMENT(S)

Reference will now be made to the exemplary embodiments, and specific language will be used herein to describe the same. It will nevertheless be understood that no limitation of the scope of the invention is thereby intended. Alterations and further modifications of the inventive features illustrated herein, and additional applications of the principles of the inventions as illustrated herein, which would occur to one skilled in the relevant art and having possession of this disclosure, are to be considered within the scope of the invention. It is also to be understood that the terminology used herein is used for the purpose of describing particular embodiments only. The terms are not intended to be limiting unless specified as such.

It must be noted that, as used in this specification and the appended claims, the singular forms "a," "an," and "the" include plural referents unless the content clearly dictates otherwise.

The term "solution" is also used throughout the specification to describe the liquid compositions of the present invention. However, as these "solutions" include colloidal transition metals, these compositions can also be described as dispersions or suspensions. As the continuous phase is typically a solution, and the transition metal is present as a colloid, for convenience, these compositions will typically be referred to as "solutions" herein.

The term "substantially free" when used with the disinfectant compositions of the present invention refers to the total absence of or near total absence of a specific compound or composition. For example, when a composition is said to be substantially free of aldehydes, there are either no aldehydes in the composition or only trace amounts of aldehydes in the composition.

Concentrations, dimensions, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, a weight ratio range of about 1 wt % to about 20 wt % should be interpreted to include not only the explicitly recited limits of 1 wt % and about 20 wt %, but also to include individual weights such as 2 wt %, 11 wt %, 14 wt %, and sub-ranges such as 10 wt % to 20 wt %, 5 wt % to 15 wt %, etc.

In accordance with this, an aqueous disinfectant or sterilant composition can comprise an aqueous vehicle, including water, from 0.001 wt % to 50 wt % of a peracid, and from 0.001 wt % to 25 wt % of a peroxide. Additionally, from 0.001 ppm to 50,000 ppm by weight of a colloidal transition metal based on the aqueous vehicle content can also be present.

In one embodiment, the disinfectant or sterilant composition can include only ingredients that are food-grade or food safe. For example, though not required, the composition can be substantially free of disinfectant ingredients commonly present in many commercially available surface cleaners. Examples of non-food-grade ingredients which can be omitted from the disinfectants or sterilants of the present invention include, but are not limited to, aldehydes such as glutaraldehyde; chlorine-based disinfectants; chlorine and bromine-based disinfectants; iodophore-based disinfectants; phenolic-based disinfectants quaternary ammonium-based disinfectants; and the like.

Optionally, the aqueous vehicle can include other ingredients, such as organic co-solvents. In particular, certain alcohols can be present. For example, alcohols, including aliphatic alcohols and other carbon-containing alcohols, having from 1 to 24 carbons ($C_1$-$C_{24}$ alcohol) can be used. It is to be noted that "$C_1$-$C_{24}$ alcohol" does not necessarily imply only straight chain saturated aliphatic alcohols, as other carbon-containing alcohols can also be used within this definition, including branched aliphatic alcohols, alicyclic alcohols, aromatic alcohols, unsaturated alcohols, as well as substituted aliphatic, alicyclic, aromatic, and unsaturated alcohols, etc. In one embodiment, the aliphatic alcohols can be $C_1$ to $C_5$ alcohols including methanol, ethanol, propanol and isopropanol, butanols, and pentanols, due to their availability and lower boiling points. This being stated, it has been discovered that polyhydric alcohols can be particularly effective in enhancing the disinfectant and sterilant potency of the compositions of the present invention, as well as provide some degree of added stabilization. Without being limited by theory, it is believed that the increased number of hydroxyl groups in the polyhydric alcohols enhance the potency of the disinfectant and sterilant solutions by interacting with the aqueous medium and the peracid, thereby stabilizing the solution. The increase in the hydroxyl groups may also increase the number of hydroxyl radicals or groups in the disinfectant/sterilant solutions, thereby further enhancing the potency or kill ability of the solutions/dispersions. Examples of polyhydric alcohols which can be used in the present invention include but are not limited to ethylene glycol (ethane-1,2-diol) glycerin (or glycerol, propane-1,2,3-triol), and propane-1,2-diol. Other non-aliphatic alcohols may also be used including, but not limited to, phenols and substituted phenols, erucyl alcohol, ricinolyl alcohol, arachidyl alcohol, capryl alcohol, capric alcohol, behenyl alcohol, lauryl alcohol (1-dodecanol), myristyl alcohol (1-tetradecanol), cetyl (or palmityl) alcohol (1-hexadecanol), stearyl alcohol (1-octadecanol), isostearyl alcohol, oleyl alcohol (cis-9-octadecen-1-ol), palmitoleyl alcohol, linoleyl alcohol (9Z,12Z-octadecadien-1-ol), elaidyl alcohol (9E-octadecen-1-ol), elaidolinoleyl alcohol (9E,12E-octadecadien-1-ol), linolenyl alcohol (9Z,12Z,15Z-octadecatrien-1-ol), elaidolinolenyl alcohol (9E,12E,15-E-octadecatrien-1-ol), combinations thereof and the like.

In some embodiments, for practical considerations, methanol, ethanol, and denatured alcohols (mixtures of ethanol and smaller amounts of methanol, and optionally, minute amounts of benzene, ketones, acetates, etc.) can often be preferred for use because of their availability and cost. If the desire is to provide a food grade composition, then alcohols can be selected that satisfy this requirement. The concentration of alcohol can vary over a wide range, such as from 0 to 95% by weight, but when present, can range from 0.001 wt % to 95 wt %, and more preferably, from 1 wt % to 50 wt %. Further, ranges of from about 5 wt % to 50 wt % can also be used, and still further, ranges from about 5 wt % to about 15 wt % can be also be used. As these ranges are merely exemplary, one skilled in the art could modify these ranges for a particular application, considering such things as whether alcohol selected for use is polyhydric, whether the alcohol is food grade, mixtures of alcohols, etc.

Regarding the transition metal, in accordance with embodiments of the present invention, the metal can be in colloidal form. In one specific embodiment, the colloidal transition metal can be in a sub-micron form (i.e. dispersion of less than 1 μm metal colloidal particles). However, larger colloidal transition metal particles can also be used in certain applications. Typical transition metals that are desirable for use include Group VI to Group XI transition metals, and more preferably, can include Group X to Group XI transition metals. Alloys including at least one metal from the Group VI to Group XI metals can also be used. It is recognized that any of these metals will typically be oxidized to the corresponding cation in the presence of a peracid. However, with colloidal metals, typically, the surface is usually more susceptible to such oxidation. Further, when colloidal metals are dispersed in a colloidal solution, there is often an amount of the metal in ionic or salt form that is also present in the suspension solution. For example, a colloidal silver may include a certain percentage of a silver salt or ionic silver in solution, e.g., 10% to 90% by weight of metal content can be ionic based on the total metal content. This being stated, certain preferred metals for use in accordance with embodiments of the present invention are ruthenium, rhodium, osmium, iridium, palladium, platinum, copper, gold, silver, alloys thereof, and mixtures thereof. Silver is often the most preferred, depending on the application, the levels of kill that are desired or required, the type of pathogen being targeted, the substrate that is being cleaned, etc. For example, if cleaning a copper instrument or surface, there may be some advantage to using copper as the transition metal rather than silver.

Any of these embodiments can also benefit from the use of alloys. For example, certain combinations of metals in an alloy may provide an acceptable kill level for a specific pathogen, and also provide benefits that are related more to a secondary consideration, such as solution stability, substrate to be cleaned, etc. Preferred examples of transition metal alloys for use in the present invention include but are not limited to copper-silver allows, silver-manganese alloys, Iron-copper alloys, chromium-silver alloys, gold-silver alloys, and magnesium-silver alloys.

The concentration of the metal content that can be present in the solution is from 0.001 ppm to 50,000 ppm by weight, based on the content of the liquid vehicle as a whole. However, in another embodiment, the concentration of metal can be from 10 ppm to 1500 ppm by weight. Exemplary colloidal silvers that can be used include those sold by Solutions IE, Inc. under the trade names CS Plus and CS Ultra. Other colloidal silver products that can be used as the silver source include ASAP, Sovereign Silver, Silver Max, and the like. In one embodiment, the colloidal particles used in the present invention can have an average particle size of from 0.001 μm to 1.0 μm. In another embodiment the colloidal transition metal particles can have an average particle size of from 0.030 μm to 0.5 μm. In still another embodiment, the average particle size can be from about 0.35 μm to 0.45 μm. Though any colloidal silver solution that is functional for use in the formulations of the present invention can be used, in one embodiment, it can be desirable to use RO water as the suspension medium for the colloidal silver that is mixed with the other ingredients. In a more detailed aspect, the RO water can also be distilled, resulting in 18-20 MΩ water, though this is not required.

The peracid (or peroxyacid) can be any aliphatic or aromatic peroxyacid that is functional for disinfectant purposes in accordance with embodiments of the present invention.

While any peroxyacid could be used, peroxyacids containing from 1 to 7 carbons are the most practical for use. These peroxyacids can include, but not be limited to, peroxyformic acid, peroxyacetic acid, peroxyoxalic acid, peroxypropanoic acid, perlactic acid, peroxybutanoic acid, peroxypentanoic acid, peroxyhexanoic acid, peroxyadipic acid, peroxycitric, and/or peroxybenzoic acid and mixtures thereof. The peroxyacid used in the present invention can be prepared using any method known in the art. When the peroxyacid is prepared from an acid and hydrogen peroxide, the resultant mixture contains both the peroxyacid and the corresponding acid that it is prepared from. For example, in embodiments that utilize peroxyacetic acid, the presence of the related acid (acetic acid) provides stability to the mixture, as the reaction is an equilibrium between the acid, hydrogen peroxide, and the peroxyacid and water, as follows:

$$H_2O_2 + CH_3COOH \leftrightarrow CH_3COO\text{—}OH + H_2O$$

The peroxyacid portion of this formulation can range from about 0.001 wt % to about 50 wt %, but ranges from 0.001 wt % to 25 wt % are considered more desirable, and ranges from 1 wt % to 10 wt % are generally more preferred.

While hydrogen peroxide is considered to be a desirable peroxide for use in accordance with embodiments of the present invention, other peroxides can also be used, such as metal peroxides and peroxyhydrates. The metal peroxides that can be used include, but are not limited to, sodium peroxide, magnesium peroxide, calcium peroxide, barium peroxide, and/or strontium peroxide. Other salts (for example sodium percarbonate) have hydrogen peroxide associated therewith much like waters of hydration, and these could also be considered to be a source of hydrogen peroxide, thereby producing hydrogen peroxide in situ. The concentrations of the peroxide portion of this formulation can range from about 0.001 wt % to 25 wt %, but ranges of from 0.001 wt % to 10 wt %, and further, from 1 wt % to 3 wt % are often adequate for use.

The compositions of the present invention can be prepared for application by any of a number of methods. For example, the composition can be prepared as a solution, gel, foam, etc. As a solution, the composition can be used as a liquid dispersion bath for dipping instruments or other objects, as a spray for applying to less mobile objects, as a wipe where the liquid dispersion is applied to a fabric or fabric-like material for easy application without the need for spray or other application methods, as a topical dressing, as a mouthwash, etc. In other words, any application method for disinfecting hard surfaces known by those skilled in the art can be utilized in accordance with embodiments of the present invention.

Additionally, though the compositions of the present invention are described primarily as general disinfectants and/or sterilants, it is recognized that there are many other possible applications. For example, without limitation, the compositions of the present invention can be used to kill bacteria, spores, viruses, parasites, funguses, and molds. As described, this powerful composition can be used against all of these types of organisms with relative to complete safety to humans and other mammals.

Because these compositions can be formulated to be very safe, e.g., including only food grade components in one embodiment, these compositions can be used in areas which extend well beyond their use as hard surface disinfectants and sterilants. Such product categories include both topically and internally applied products for both humans and animals. For example, these compositions can be used for antiseptics, burn treatments, diaper rash products, and various skin care products. Alternatively, these compositions can be used inside the mouth, such as for mouth washes, tooth pastes, and various other disinfecting solutions that are be employed in dental mold materials. As dental molds are known to spread significant disease in the dental industry, such use with dental molds can prevent or reduce the spread of pathogens from a patient's mouth to lab employees working with the finished molds. Still a further category of use includes application for antibiotic and antiviral purposes. These compositions can be formulated into lozenges or gums for application to the mouth and throat, and can even be administered orally, intramuscularly, intravenously, etc. Because of the kill levels that can be achieved, even when formulated with only food grade components, a wide range of pathogens, as well as some viruses, can be killed internally. Without being bound by any particular possibility, these compositions can be useful in killing various viruses such as HIV, SARS, West Nile, Bird Flu, and others.

EXAMPLES

The following examples illustrate the embodiments of the invention that are presently best known. However, it is to be understood that the following are only exemplary or illustrative of the application of the principles of the present invention. Numerous modifications and alternative compositions, methods, and systems may be devised by those skilled in the art without departing from the spirit and scope of the present invention. The appended claims are intended to cover such modifications and arrangements. Thus, while the present invention has been described above with particularity, the following examples provide further detail in connection with what are presently deemed to be the most practical and preferred embodiments of the invention.

Example 1

Preparation of Disinfectant

An aqueous disinfectant composition is prepared in accordance with embodiments of the present invention, which includes the following ingredients in approximate amounts:
 85 wt % distilled water containing 600 ppm by weight colloidal silver;
 9 wt % ethanol; and
 6 wt % peroxyacetic acid.
To the composition is added a small amount, i.e. <3 wt % based on the aqueous composition as a whole, of hydrogen peroxide to stabilize the peroxyacetic acid. It is noted that there will be less than 600 ppm by weight of the colloidal silver when based on the aqueous vehicle content as a whole.

Example 2

Preparation of Disinfectant

An aqueous disinfectant composition is prepared in accordance with embodiments of the present invention, which includes the following ingredients in approximate amounts:
 85 wt % distilled water containing 600 ppm by weight colloidal silver;
 9 wt % n-propanol; and
 6 wt % peroxyacetic acid.
To the composition is added a small amount, i.e. <3 wt % based on the aqueous composition as a whole, of hydrogen peroxide to stabilize the peroxyacetic acid. It is noted that there will be less than 600 ppm by weight of the colloidal silver when based on the aqueous vehicle content as a whole.

Example 3

Preparation of Disinfectant

An aqueous disinfectant composition is prepared in accordance with embodiments of the present invention, which includes the following ingredients in approximate amounts:

75 wt % RO water (reverse osmosis water) containing 1500 ppm by weight colloidal silver;
15 wt % ethanol; and
10 wt % peroxyacetic acid.

To the composition is added a small amount of hydrogen peroxide and acetic acid to the solution to stabilize the peracetic acid. It is noted that there will be less than 1500 ppm by weight of the colloidal silver when based on the aqueous vehicle content as a whole.

Example 4

Preparation of Disinfectant

An aqueous disinfectant composition is prepared in accordance with embodiments of the present invention, which includes the following ingredients in approximate amounts:

75 wt % distilled water containing 10,000 ppm by weight colloidal silver;
20 wt % denatured alcohol; and
5 wt % peroxyformic acid.

Small amounts of hydrogen peroxide and formic acid are also added to the composition as a whole to stabilize the peroxyformic acid. It is noted that there will be less than 10000 ppm by weight of the colloidal silver when based on the aqueous vehicle content as a whole.

Example 5

Preparation of Disinfectant

An aqueous disinfectant composition is prepared in accordance with embodiments of the present invention, which includes the following ingredients in approximate amounts:

85 wt % distilled water containing 80 ppm by weight colloidal silver;
9 wt % ethanol; and
6 wt % peroxyacetic acid.

To the composition is added a small amount, i.e. <3 wt % based on the aqueous composition as a whole, of hydrogen peroxide to stabilize the peroxyacetic acid. It is noted that there will be less than 80 ppm by weight of the colloidal silver when based on the aqueous vehicle content as a whole.

Example 6

Kill-Time Studies of *Staphylococcus aureus* Using Disinfectant of Example 1

A study was conducted to determine the antimicrobial activity of the colloidal silver-containing disinfectant of Example 1, when challenged with an organic load, on the test organism *Staphylococcus aureus*. This was accomplished by performing a standard suspension test on the disinfectant containing 5% v/v horse serum. A 15 second contact time was evaluated.

Specifically, the test suspension was prepared by growing a 5 ml culture of *Staphylococcus aureus*, ATCC 6538, in Todd Hewitt Broth at 37° C., for 20 hours. Five (5) ml of culture was pelleted by centrifugation, washed with 5 ml sterile 18 MΩ water, centrifuged again, and resuspended in a final volume of 5 ml sterile water.

A neutralizer was prepared that consisted of 9 ml tubes of 12.7 wt % Tween 80 (surfactant), 6.0 wt % Tamol, 1.7 wt % lecithin, 1 wt % peptone, and 0.1 wt % cystine, to which was added 10 pd of catalase solution (Sigma, C100, 42,300 units/mg).

The "Kill Time" procedure followed was as follows: A 9.9 ml aliquot of the disinfectant of Example 1 (containing 5% v/v horse serum) was placed in a sterile 20 mm×150 mm tube, and the tube was equilibrated in a 20° C. water bath. The tube of disinfectant was inoculated with 100 μl of the test organism suspension at time zero. After 15 seconds, 1 ml of the organism/disinfectant suspension was removed to 9 ml of neutralizer. After 2 minutes, the neutralized suspension was serially diluted ($1:1\times10$, $1:1\times10^2$, $1:1\times10^3$, etc.) in physiological saline solution (PSS). The number of viable organisms in selected dilution tubes was assayed by membrane filtration. One (1) ml aliquots were plated in duplicate, and the membranes were washed with about 100 ml of sterile PSS and removed to Columbia agar plates. The plates were incubated at 37° C. for 20 hours. The number of colonies on each filter was counted and log reduction and percent kill values were computed.

As a control, a titer (or measurement of the amount or concentration of a substance in a solution) of the test suspension was computed by performing membrane filtration assays of selected 1:10 dilutions of the test suspension in PSS. A neutralizer control was performed by inoculating a mixture of 9 ml of neutralizer and 1 ml of disinfectant with 100 μl of the $1:10^5$ dilution of the titer. This produced about 1,500 CFU/ml in the tube, which was allowed to stand for 20 minutes prior to dilution and assay of the tubes by membrane filtration using duplicate 1 ml samples. Sterilization controls were performed by filtering 100 ml (PSS) or 1 ml (other fluids) samples of each solution used in this testing. Plates were incubated as above.

The results are provided as follows:

TABLE 1a

| | Titer | | |
|---|---|---|---|
| Dilution | $1:1\times10^5$ | $1:1\times10^6$ | $1:1\times10^7$ |
| Number of | TNC* | TNC | 111 |
| Colonies | TNC | TNC | 89 |

*TNC—Too Numerous to Count

TABLE 1b

| Disinfectant solution (Example 1 solution with 5% v/v horse serum) Dilution of *staphylococcus*/disinfectant suspension | | | |
|---|---|---|---|
| Dilution | $1:1\times10^1$ | $1:1\times10^2$ | $1:1\times10^3$ |
| 15 Seconds | 0 | 0 | 0 |
| | 0 | 0 | 0 |

TABLE 1c

| Neutralization control | | |
| --- | --- | --- |
| Dilution | undilute | $1:1 \times 10^1$ |
| 15 Seconds | TNC | 156 |
| | TNC | 148 |

Sterilization controls indicated zero growth for the neutralizer, water, PSS, Columbia agar, disinfectant, and horse serum. Results of the titer showed a viable *staphylococcus* concentration of $1 \times 10^{10}$ organisms per ml in the original suspension. Inoculation of 9.9 ml of disinfectant with 100 μl of this suspension produced an initial concentration of $1 \times 10^8$ organisms per ml in the assay tube. Results from these procedures allowed log reduction (LR) and percent kill (PK) values to be calculated using the formulas: 1) LR=−Log(S/So) where S=concentration of viable organisms after 45 minutes; and So=the initial concentration of viable organisms at time zero; and 2) PK=(1−(S/So))×100. These values are shown below.

TABLE 2

| | | Results | |
| --- | --- | --- | --- |
| Solution | Contact Time | Log Reduction (LR) | Percent Kill (PK) |
| Disinfectant solution of Example 1 with 5% v/v horse serum | 15 sec | >7.00 | >99.99999 |

The neutralization control data indicated that the test solution was adequately neutralized. Observed counts were slightly greater than those expected, indicating no residual killing took place due to un-neutralized disinfectant. In general, the disinfectant solution tested here had high antimicrobial activity against *Staphylococcus aureus*. It is significant to note that this level of activity was achieved even though the disinfectant was premixed with an organic load consisting of 5% v/v horse serum. An organic load (such as 5% v/v horse serum) will often adversely affect the antimicrobial action of disinfectants. The solution of Example 1 was nevertheless able to effect greater than a 7 log reduction of viable organisms within 15 seconds, even in the presence of 5% v/v horse serum.

Example 7

Kill-Time Studies of *Staphylococcus aureus* Using Lysol® Spray

A study was conducted to determine the antimicrobial activity of a Lysol® spray disinfectant on the test organism *Staphylococcus aureus*. This was accomplished by performing a standard suspension test. A 15 second contact time was evaluated.

Specifically, a test organism in the form of a test suspension was prepared by growing a 5 ml culture of *Staphylococcus aureus*, ATCC 6538 in Todd Hewitt Broth at 37° C., for 20 hr. Five (5) ml of culture was pelleted by centrifugation, washed with five ml sterile 18 MΩ water, centrifuged again, and resuspended in a final volume of five ml sterile water.

A neutralizer was also prepared that consisted of 9 ml tubes of 12.7 wt % Tween 80, 6.0 wt % Tamol, 1.7 lecithin, 1 wt % peptone, and 0.1 wt % cystine.

The "Kill Time" procedure followed was as follows: A 9.9 ml aliquot of the disinfectant (Lysol® Brand II Disinfectant, Spring Waterfall Scent, Lot #B4194-NJ2; 1413-A3) was placed in a sterile 20 mm×150 mm tube. The tube was equilibrated in a 20° C. water bath. The tube of disinfectant was inoculated with 100 μl of the test organism suspension at time zero. After 15 seconds, 1 ml of organism/disinfectant suspension was removed to 9 ml of neutralizer. After 2 minutes, the neutralized suspension was serially diluted ($1:1 \times 10$, $1:1 \times 10^2$, $1:1 \times 10^3$, etc.) in physiological saline solution (PSS). The number of viable organisms in selected dilution tubes was assayed by membrane filtration. One (1) ml aliquots were plated in duplicate. The membranes were washed with about 100 ml of sterile PSS and removed to Columbia agar plates. The plates were incubated at 37° C. for 20 hours. The number of colonies on each filter was counted and log reduction and percent kill values were computed.

As a control, a titer of the test suspension was computed by performing membrane filtration assays of selected 1:10 dilutions of the test suspension in PSS. A neutralizer control was performed by inoculating a mixture of 9 ml of neutralizer and 1 ml of disinfectant with 100 μl of the $1:10^5$ dilution of the titer. This produced about 1,500 CFU/ml in the tube, which was allowed to stand for 20 minutes prior to dilution and assay of the tubes by membrane filtration using duplicate 1 ml samples. Sterilization controls were performed by filtering 100 ml (PSS) or 1 ml (other fluids) samples of each solution used in this testing. Plates were incubated as above.

The results are provided as follows:

TABLE 3a

| | Titer | | |
| --- | --- | --- | --- |
| Dilution | $1:1 \times 10^5$ | $1:1 \times 10^6$ | $1:1 \times 10^7$ |
| Number of Colonies | TNC* TNC | 127 167 | 15 13 |

*TNC—Too Numerous to Count

TABLE 3b

| Disinfectant solution (Lysol ® Spray) | | |
| --- | --- | --- |
| Dilution of *staphylococcus*/disinfectant suspension | | |
| Dilution | $1:1 \times 10^1$ | $1:1 \times 10^2$ | $1:1 \times 10^3$ |
| 15 Seconds | 0 0 | 0 0 | 0 0 |

TABLE 3c

| Neutralization control | | |
| --- | --- | --- |
| Dilution | Undilute | $1:1 \times 10^1$ |
| 15 Seconds | TNC | 76 |
| | TNC | 72 |

Sterilization controls indicated zero growth for the neutralizer, water, PSS, Columbia agar, and disinfectant. Results of the titer showed a viable *staphylococcus* concentration of $1.47 \times 10^9$ organisms per ml in the original suspension. Inoculation of 9.9 ml of disinfectant with 100 μl of this suspension produced an initial concentration of $1.47 \times 10^7$ organisms per ml in the assay tube. Results from these procedures allowed log reduction (LR) and percent kill (PK) values to be calculated using the formulas: 1) LR=−Log(S/So) where S=concentration of viable organisms after 45 minutes; and So=the initial concentration of viable organisms at time zero; and 2) PK=(1−(S/So))×100.

These values are shown in Table 4 below.

TABLE 4

| Results | | | |
|---|---|---|---|
| Solution | Contact Time | Log Reduction (LR) | Percent Kill (PK) |
| Lysol ® Spray | 15 sec | >6.17 | >99.99993 |

The neutralization control data indicated that each test solution was adequately neutralized. Observed counts were slightly greater than those expected, indicating no residual killing took place due to un-neutralized disinfectant. In general, Lysol® Spray had high antimicrobial activity against *Staphylococcus aureous*. It was able to effect greater than a 6-log reduction of viable organisms within 15 seconds. As a note, this test was conducted without the horse serum organic load of Example 5.

In accordance with the present comparative example using Lysol®, it is to be noted that this example is a suspension example conducted in an enclosed environment. Because of the large amount of alcohol in Lysol®, Lysol® performs much better in the enclosed environment when compared to a typical open air use on a hard surface. Conversely, the compositions prepared in accordance with embodiments of the present invention, which can include a majority of water (which evaporates much less rapidly than alcohol), perform more similarly in suspension examples compared to open air hard surface applications. Thus, the comparison of the present Lysol® example to Example 6 shows Lysol® activity in a much more favorable light then would be present in actual use. For example, Reckitt Benckiser, who manufactures Lysol® products, advertises in their own Literature that Lysol® is able to kill 99.9% (3 $Log_{10}$ reduction) of bacteria (including *Staphylococcus aureous* (MRSA)) in 30 seconds, whereas the present suspension example shows a kill level of 99.9999% (6 $Log_{10}$ reductions) of *Staphylococcus* aureous in 15 seconds.

Example 8

Kill-Time Studies of Sporicidal Activity Using Disinfectant of Example 1

A study was conducted to determine the antimicrobial activity of the silver-containing disinfectant of Example 1 on bacterial endospores from the test organism *Bacillus subtilis*. This was accomplished by performing a standard kill-time suspension test using a suspension of *B. subtilis* endospores. In general, spores are much more difficult to kill than common bacteria.

The test organism in the form of a test suspension was prepared containing endospores from *Bacillus subtilis* (ATCC #19659). The endospores were specifically prepared from a culture grown on Nutrient agar, to which additional sporulation enhancements were added. Plates were harvested with sterile water and endospores were purified by repeated centrifugations and resuspensions in water. The final wash was in 70 wt % ethanol for 30 minutes, to ensure the death of all vegetative bacteria. The spores were resuspended in water containing 0.1 wt % Tween 80 to prevent clumping and stored at 4° C. until used.

A neutralizer solution was also prepared that consisted of 9 ml tubes of 12.7 wt % Tween 80, 6.0 wt % Tamol, 1.7 wt % lecithin, 1 wt % peptone, and 0.1 wt % cystine, to which 10 µl of catalase solution (Sigma, C100, 42,300 units/mg) was added immediately before use.

The "kill time" procedure was as follows: A 9.9 ml aliquot of the disinfectant was placed in a sterile glass culture tube. The tube was equilibrated in a 20° C. water bath. The tube of disinfectant was inoculated with 100 µl of the spore suspension at time zero. After 1 hour, 1 ml of spore/disinfectant suspension was removed to 9 ml of neutralizer. The tube was mixed thoroughly. After 2 minutes, the neutralized suspension was serially diluted (1:1×10, 1:1×$10^2$, 1:1×$10^3$, etc.) in physiological saline solution (PSS). The number of viable spores in selected dilution tubes was assayed by membrane filtration. One (1) ml aliquots were plated in duplicate. The membranes were washed with about 100 ml of sterile PSS and removed to Columbia agar plates. The plates were incubated at 37° C. for 20 hours. The number of colonies on each filter was counted and log reduction and percent kill values were computed.

As a control, a titer of the test suspension was computed by performing membrane filtration assays on selected 1:10 dilutions in PSS of the test suspension. A neutralizer control was performed by inoculating a mixture of 9 ml of neutralizer and 1 ml of disinfectant with 100 µl of the 1:1×$10^5$ dilution of the titer. This produced about 200 CFU/ml in the tube, which was allowed to stand for 20 minutes prior to dilution and assay by membrane filtration using duplicate 1 ml samples.

The results are provided as follows:

TABLE 5a

| | Titer | | |
|---|---|---|---|
| Dilution | 1:1 × $10^6$ | 1:1 × $10^7$ | 1:1 × $10^8$ |
| Number of Colonies | TNC* TNC | 210 37 | 8 14 |

*TNC—Too Numerous to Count

TABLE 5b

| Disinfectant solution (Example 1) | | | |
|---|---|---|---|
| Dilution of *B. subtilis* spores/disinfectant suspension | | | |
| Dilution | 1:1 × $10^2$ | 1:1 × $10^3$ | 1:1 × $10^4$ |
| 5 minutes | 13 18 | 4 2 | 0 0 |

TABLE 5c

| Disinfectant solution (Example 1) | | | | |
|---|---|---|---|---|
| Dilution of *B. subtilis* spores/disinfectant suspension | | | | |
| Dilution | 1:1 × $10^1$ | 1:1 × $10^2$ | 1:1 × $10^3$ | 1:1 × $10^4$ |
| 10 minutes | 24 37 | 2 2 | 0 1 | 0 0 |

TABLE 5d

Disinfectant solution (Example 1)
Dilution of *B. subtilis* spores/disinfectant suspension

| Dilution | $1:1 \times 10^1$ | $1:1 \times 10^2$ | $1:1 \times 10^3$ |
|---|---|---|---|
| 15 minutes | 0 | 0 | 0 |
|  | 0 | 0 | 0 |

TABLE 5e

Neutralization control

| Dilution | undilute | $1:1 \times 10^1$ |
|---|---|---|
| 15 Seconds | 185 | 12 |
|  | 214 | 25 |

Sterilization controls indicated zero growth for the water, PSS, Columbia agar, and disinfectant. Results of the titer showed a viable *B. subtilis* spore concentration of $1.24 \times 10^9$ spores per ml in the original suspension. Inoculation of 9.9 ml of disinfectant with 100 µl of this suspension produced an initial concentration of $1.24 \times 10^7$ spores per ml in the assay tube. Results from these procedures allowed log reduction (LR) and percent kill (PK) values to be calculated using the formulas: 1) $LR = -Log(S/So)$ where S=concentration of viable organisms after 1 hour, and So=the initial concentration of viable organisms at time zero; and 2) $PK = (1-(S/So)) \times 100$. These values are shown below in Table 6.

TABLE 6

Results

| Solution | Contact Time | Log Reduction (LR) | Percent Kill (PK) |
|---|---|---|---|
| Example 1 | 5 min | 3.90 | 99.9875 |
| Example 1 | 10 min | 4.61 | 99.9975 |
| Example 1 | 15 min | >6.09 | 99.99992 |

Neutralization control data revealed that the neutralizer was able to adequately neutralize this disinfectant. Observed counts were greater than those expected. The solution of Example 1 had relatively high sporicidal activity, producing greater than a 6-log reduction within 15 minutes. *B. subtilis* is a common species used in sporicidal testing and belongs to the same genus as the organism that causes anthrax. In other words, because of their genetic similarities, *B. subtilis* spores have been used as non-pathogenic surrogates for spores of *Bacillus anthracis*.

Example 9

Kill-Time Studies of *Francisella tularensis* Using Disinfectant of Example 2

A study was conducted to determine the antimicrobial activity of the silver-containing disinfectant of Example 2 on *Francisella tularensis* bacteria, the etiologic agent of tularemia. This was accomplished by performing a standard kill-time suspension test using a suspension of fully virulent *F. tularensis* bacteria. As the organism is a CDC select agent, all tests were performed in a Biosafety Level 3 (BSL-3) laboratory by personnel trained in BSL-3 practices and procedures.

The test organism in the form of a test suspension was prepared containing *F. tularensis* bacteria (isolate#: 02-1103a). The suspension was prepared as follows: Four Trypticase Soy Agar plates with 0.1% cysteine and 5% sheep blood (TSACB) were lawn-inoculated from isolated colonies on a production plate that had been gram-stained to insure purity. The plates were incubated at 37° C. for 48 hours. The growth on each of four plates was scraped into suspension using three ml of physiological saline solution (PSS) and a bent loop. The suspension was pipetted into a 50 ml conical centrifuge tube. Suspensions from all four plates were collected into a single tube. The tube was centrifuged in an aerosol tight rotor at 3,845×g for seven minutes. The supernatant solution was removed and the pellet was re-suspended in 4 ml of PSS. The suspension was held at 4° C. until used.

A neutralizer solution was also prepared that consisted of 9 ml tubes of 12.7 wt % Tween 80, 6.0 wt % Tamol, 1.7 wt % lecithin, 1 wt % peptone, 1.0 wt % cysteine, and 500 mM Tris (pH 7.7), to which 100 µl of catalase solution (Sigma, C100, 42,300 units/mg) was added immediately before use.

The "kill time" procedure was as follows: A 9.9 ml aliquot of the disinfectant described in Example 2 was placed in a sterile glass culture tube. The tube was equilibrated in a 20° C. water bath. The tube of disinfectant was inoculated with 1.0 ml of the test organism suspension at time zero. After 15 seconds and 30 seconds 1 ml of test organism/disinfectant suspension was removed to 9 ml of neutralizer. The tube was mixed thoroughly. After 2 minutes, the neutralized suspension was serially diluted (1:10, $1:1 \times 10^2$, $1:1 \times 10^3$, etc.) in physiological saline solution (PSS). The number of viable spores in selected dilution tubes was assayed by membrane filtration. One (1) ml aliquots were plated in duplicate. The membranes were washed with about 100 ml of sterile PSS and removed to TSACB agar plates. The plates were incubated at 37° C. for 72 hours. The number of colonies on each filter was counted and log reduction and percent kill values were computed.

As a control, a titer of the test suspension was computed by performing membrane filtration assays on selected 1:10 dilutions in PSS of the test suspension. A neutralizer control was performed by inoculating a mixture of 9 ml of neutralizer and 1 ml of disinfectant with 100 µl of the $1:1 \times 10^5$ dilution of the titer. This produced about 7,110 colony forming units (CFU)/ml in the tube, which was allowed to stand for 20 minutes prior to dilution and assay by membrane filtration using duplicate 1 ml samples.

The results are provided as follows:

TABLE 7a

Titer

| Dilution | $1:1 \times 10^6$ | $1:1 \times 10^7$ | $1:1 \times 10^8$ | $1:1 \times 10^9$ |
|---|---|---|---|---|
| Number of Colonies | TNC* | TNC | TNC | 68 |
|  | TNC | TNC | TNC | 77 |

*TNC—Too Numerous to Count

TABLE 7b

Disinfectant solution (Example 2)
Dilution of *F. tularensis*/disinfectant suspension

| Dilution | $1:1 \times 10^1$ | $1:1 \times 10^2$ |
|---|---|---|
| 15 Seconds | 0 | 0 |
|  | 0 | 0 |
| 30 Seconds | 0 | 0 |
|  | 0 | 0 |

TABLE 7c

| Neutralization control | |
| --- | --- |
| Undiluted | 1:10 |
| TNC | 588 |
| TNC | 558 |

Results of the titer showed a viable *F. tularensis* concentration of $7.25 \times 10^{10}$ CFU per ml in the original suspension. Inoculation of 9.0 ml of disinfectant with 1.0 ml of this suspension produced an initial concentration of $7.25 \times 10^9$ CFU per ml in the assay tube. Results from these procedures allowed log reduction (LR) and percent kill (PK) values to be calculated using the formulas: 1) LR=−Log(S/So) where S=concentration of viable organisms after the specified contact time, and So=the initial concentration of viable organisms at time zero; and 2) PK=(1−(S/So))×100. These values are shown below in Table 8.

TABLE 8

Results

| Solution | Contact Time | Log Reduction (LR) | Percent Kill (PK) |
| --- | --- | --- | --- |
| Example 2 | 15 Seconds | >8.86 | 99.99999986 |
| Example 2 | 30 Seconds | >8.86 | 99.99999986 |

Neutralization control data revealed counts that were similar to those expected; a mean of 573 CFU were obtained and about 711 CFU were expected. This indicates that the neutralizer solution employed successfully neutralized the disinfectant solution in these tests. The solution demonstrated a relatively rapid kill rate of *F. tularensis*. It was able to produce greater than an eight-log reduction within 15 seconds, which was complete kill in the system employed.

Example 10

Kill-Time Studies of *Yersinia pestis* Using the Disinfectant of Example 2

A study was conducted to determine the antimicrobial activity of the silver-containing disinfectant of Example 2 on *Yersinia pestis* bacteria, the etiologic agent of plague. This was accomplished by performing a standard kill-time suspension test using a suspension of fully virulent *Y. pestis* bacteria. As the organism is a CDC select agent, all tests were performed in a Biosafety Level 3 (BSL-3) laboratory by personnel trained in BSL-3 practices and procedures.

The test organism in the form of a test suspension containing *Y. pestis* bacteria (isolate#: 83-1880a) was prepared as follows: Four Columbia Agar plates were lawn-inoculated from isolated colonies on a production plate that had been gram-stained to insure purity. The plates were incubated at 28° C. with 5% $CO_2$ for 48 hours. The growth on each of four plates was scraped into suspension using three ml of physiological saline solution (PSS) and a bent loop. The suspension was pipetted into a 50 ml conical centrifuge tube. Each plate was rinsed with an additional two ml of PSS, which was also added to the 50 ml tube. Suspensions from all four plates were collected into a single tube. The tube was centrifuged in an aerosol tight rotor at 3,845×g for seven minutes. The supernatant solution was removed and the pellet was re-suspended in 4 ml of PSS. The suspension was held at 4° C. until used.

A neutralizer solution was also prepared that consisted of 9 ml tubes of 12.7 wt % Tween 80, 6.0 wt % Tamol, 1.7 wt % lecithin, 1 wt % peptone, 1.0 wt % cysteine, and 500 mM Tris (pH 7.7), to which 100 μl of catalase solution (Sigma, C100, 42,300 units/mg) was added immediately before use.

The "kill time" procedure was as follows: A 9.9 ml aliquot of the disinfectant described in Example 2 was placed in a sterile glass culture tube. The tube was equilibrated in a 20° C. water bath. The tube of disinfectant was inoculated with 1.0 ml of the test organism suspension at time zero. After 15 seconds and 30 seconds 1 ml of test organism/disinfectant suspension was removed to 9 ml of neutralizer. The tube was mixed thoroughly. After 2 minutes, the neutralized suspension was serially diluted (1:10, $1:1 \times 10^2$, $1:1 \times 10^3$, etc.) in physiological saline solution (PSS). The number of viable spores in selected dilution tubes was assayed by membrane filtration. One (1) ml aliquots were plated in duplicate. The membranes were washed with about 100 ml of sterile PSS and removed to Columbia agar plates. The plates were incubated at 37° C. with 5% $CO_2$ for 48 hours. The number of colonies on each filter was counted and log reduction and percent kill values were computed.

As a control, a titer of the test suspension was computed by performing membrane filtration assays on selected 1:10 dilutions in PSS of the test suspension. A neutralizer control was performed by inoculating a mixture of 9 ml of neutralizer and 1 ml of disinfectant with 100 μl of the $1:1 \times 10^5$ dilution of the titer. This produced about 3,380 colony forming units (CFU)/ml in the tube, which was allowed to stand for 20 minutes prior to dilution and assay by membrane filtration using duplicate 1 ml samples.

The results are provided as follows:

TABLE 9a

| | Titer | | | |
| --- | --- | --- | --- | --- |
| Dilution | $1:1 \times 10^6$ | $1:1 \times 10^7$ | $1:1 \times 10^8$ | $1:1 \times 10^9$ |
| Number of Colonies | TNC* | TNC | 260 | 31 |
| | TNC | TNC | 267 | 38 |

*TNC—Too Numerous to Count

TABLE 9b

Disinfectant solution (Example 2)
Dilution of *Y. pestis*/disinfectant suspension

| Dilution | $1:1 \times 10^1$ | $1:1 \times 10^2$ |
| --- | --- | --- |
| 15 Seconds | 0 | 0 |
| | 0 | 0 |
| 30 Seconds | 0 | 0 |
| | 0 | 0 |

TABLE 9c

| Neutralization control | |
| --- | --- |
| Undiluted | 1:10 |
| TNC | 53 |
| TNC | 60 |

Results of the titer showed a viable *Y. pestis* concentration of $3.45 \times 10^{10}$ CFU per ml in the original suspension. Inoculation of 9.0 ml of disinfectant with 1.0 ml of this suspension produced an initial concentration of $3.45 \times 10^9$ CFU per ml in the assay tube. Results from these procedures allowed log reduction (LR) and percent kill (PK) values to be calculated using the formulas: 1) LR=−Log(S/So) where S=concentration of viable organisms after the specified contact time, and So=the initial concentration of viable organisms at time zero; and 2) PK=(1−(S/So))×100. These values are shown below in Table 10.

TABLE 10

Results

| Solution | Contact Time | Log Reduction (LR) | Percent Kill (PK) |
|---|---|---|---|
| Example 2 | 15 Seconds | >8.54 | 99.9999997 |
| Example 2 | 30 Seconds | >8.54 | 99.9999997 |

Neutralization control data revealed counts that were similar to those expected; a mean of 57 CFU were obtained and about 338 CFU were expected. As this same neutralizer formulation successfully neutralized the disinfectant of Example 2 in tests with other organisms, studies were initiated to discover any *Y. pestis*-specific toxicity that might be inherent in this neutralizer. The disinfectant of Example 2 demonstrated a relatively rapid kill rate of *Y. pestis*. It was able to produce greater than eight-log reduction within 15 seconds, which was complete kill in the system employed.

Example 11

Kill-Time Studies of *Brucella abortus* Using the Disinfectant of Example 2

A study was conducted to determine the antimicrobial activity of the silver-containing disinfectant of Example 2 on *Brucella abortus* bacteria, the etiologic agent of undulant fever or brucellosis. This was accomplished by performing a standard kill-time suspension test using a suspension of fully virulent *B. abortus* bacteria. As the organism is a CDC select agent, all tests were performed in a Biosafety Level 3 (BSL-3) laboratory by personnel trained in BSL-3 practices and procedures.

The test organism in the form of a test suspension containing *B. abortus* bacteria (698 strain 544) was prepared as follows: Four *Brucella* Blood Agar (BBA) plates were lawn-inoculated from isolated colonies on a production plate that had been gram-stained to insure purity. The plates were incubated at 37° C. with 5% $CO_2$ for 48 hours. The growth on each of four plates was scraped into suspension using three ml of physiological saline solution (PSS) and a bent loop. The suspension was pipetted into a 50 ml conical centrifuge tube. Each plate was rinsed with an additional two ml of PSS, which was also added to the 50 ml tube. Suspensions from all four plates were collected into a single tube. The tube was centrifuged in an aerosol tight rotor at 3,845×g for seven minutes. The supernatant solution was removed and the pellet was re-suspended in 4 ml of PSS. The suspension was held at 4° C. until used.

A neutralizer solution was also prepared that consisted of 9 ml tubes of 12.7 wt % Tween 80, 6.0 wt % Tamol, 1.7 wt % lecithin, 1 wt % peptone, 1.0 wt % cysteine, and 500 mM Tris (pH 7.7), to which 100 µl of catalase solution (Sigma, C100, 42,300 units/mg) was added immediately before use.

The "kill time" procedure was as follows: A 9.9 ml aliquot of the disinfectant described in Example 2 was placed in a sterile glass culture tube. The tube was equilibrated in a 20° C. water bath. The tube of disinfectant was inoculated with 1.0 ml of the test organism suspension at time zero. After 15 seconds and 30 seconds 1 ml of test organism/disinfectant suspension was removed to 9 ml of neutralizer. The tube was mixed thoroughly. After 2 minutes, the neutralized suspension was serially diluted (1:10, $1:1\times10^2$, $1:1\times10^3$, etc.) in physiological saline solution (PSS). The number of viable spores in selected dilution tubes was assayed by membrane filtration. One (1) ml aliquots were plated in duplicate. The membranes were washed with about 100 ml of sterile PSS and removed to Columbia agar plates. The plates were incubated at 37° C. with 5% $CO_2$ for 48 hours. The number of colonies on each filter was counted and log reduction and percent kill values were computed.

As a control, a titer of the test suspension was computed by performing membrane filtration assays on selected 1:10 dilutions in PSS of the test suspension. A neutralizer control was performed by inoculating a mixture of 9 ml of neutralizer and 100 ml of disinfectant with 100 µl of the $1:1\times10^6$ dilution of the titer. This produced about 290 colony forming units (CFU)/ml in the tube, which was allowed to stand for 20 minutes prior to dilution and assay by membrane filtration using duplicate 1 ml samples.

The results are provided as follows:

TABLE 11a

| | Titer | | |
|---|---|---|---|
| Dilution | $1:1\times10^7$ | $1:1\times10^8$ | $1:1\times10^9$ |
| Number of Colonies | TNC* | 260 | 290 |
| | TNC | 267 | 301 |

*TNC—Too Numerous to Count

TABLE 11b

Disinfectant solution (Example 2)
Dilution of *B. abortus*/disinfectant suspension

| Dilution | $1:1\times10^1$ | $1:1\times10^2$ |
|---|---|---|
| 15 Seconds | 1 | 0 |
| | 0 | 0 |
| 30 Seconds | 0 | 0 |
| | 0 | 0 |

TABLE 11c

Neutralization control

| Undiluted | 1:10 |
|---|---|
| TNC | 200 |
| TNC | 183 |

Results of the titer showed a viable *B. abortus* concentration of $2.96\times10^{11}$ CFU per ml in the original suspension. Inoculation of 9.0 ml of disinfectant with 1.0 ml of this suspension produced an initial concentration of $2.96\times10^{10}$ CFU per ml in the assay tube. Results from these procedures allowed log reduction (LR) and percent kill (PK) values to be calculated using the formulas: 1) LR=−Log(S/So) where S concentration of viable organisms after the specified contact time, and So=the initial concentration of viable organisms at time zero; and 2) PK=(1−(S/So))×100. These values are shown below in Table 12.

TABLE 12

| | | Results | |
|---|---|---|---|
| Solution | Contact Time | Log Reduction (LR) | Percent Kill (PK) |
| Example 2 | 15 Seconds | >9.74 | 99.99999997 |
| Example 2 | 30 Seconds | >9.74 | 99.99999997 |

Neutralization control data revealed counts that were similar to those expected; a mean of 1,915 CFU were obtained and about 290 CFU were expected. This indicates that the neutralization solution employed successfully neutralized the disinfectant of Example 2 in these tests. The disinfectant of Example 2 demonstrated a relatively rapid kill rate of *B. abortus*. It was able to produce greater than nine-log reduction within 15 seconds, which was nearly complete kill in the system employed.

Example 12

Kill-Time Studies of *Bacillus anthracis* Using the Disinfectant of Example 2

A study was conducted to determine the antimicrobial activity of the silver-containing disinfectant of Example 2 on bacterial endospores from the test organism *Bacillus anthracis* bacteria. This was accomplished by performing a standard kill-time suspension test using purified endospores from a fully virulent B anthracis isolate. Because large concentrations of virulent spores were used, all tests were performed in a Biosafety Level 3 (BSL-3) laboratory by personnel trained in BSL-3 practices and procedures.

The test organism in the form of a test suspension containing endospores from B anthracis (A0256) was prepared from four 250 ml cultures grown in Leighton Doi medium in 2 L Ehrlenmeyer flasks. The flasks were shaken at 100 RPM at 37° C. for 3-5 days until 90% sporulation was achieved, as monitored by phase-contrast microscopy. Spores were harvested and washed three times with sterile HPLC water, and stored at 4° C. overnight. Three additional washes were performed, allowing the suspension to stand at 4° C. overnight between each wash. The spores were re-suspended in a total of 80 ml of sterile HPLC water until used.

A neutralizer solution was also prepared that consisted of 9 ml tubes of 12.7 wt % Tween 80, 6.0 wt % Tamol, 1.7 wt % lecithin, 1 wt % peptone, 1.0 wt % cystine, and 500 mM Tris (pH 7.7), to which 100 µl of catalase solution (Sigma, C100, 42,300 units/mg) was added immediately before use.

The "kill time" procedure was as follows: A 4.5 ml aliquot of the disinfectant described in Example 2 was placed in a sterile glass culture tube. The tube was equilibrated in a 20° C. water bath. The tube of disinfectant was inoculated with 0.5 ml of the spore suspension at time zero. After 15 seconds and 30 seconds 1 ml of spore/disinfectant suspension was removed to 9 ml of neutralizer. The tube was mixed thoroughly. After 2 minutes, the neutralized suspension was serially diluted (1:10, $1:1 \times 10^2$, $1:1 \times 10^3$, etc.) in physiological saline solution (PSS). The number of viable spores in selected dilution tubes was assayed by membrane filtration. One (1) ml aliquots were plated in duplicate. The membranes were washed with about 100 ml of sterile PSS and removed to Columbia agar plates. The plates were incubated at 37° C. for 20 hours. The number of colonies on each filter was counted and log reduction and percent kill values were computed.

As a control, a titer of the test suspension was computed by performing membrane filtration assays on selected 1:10 dilutions in PSS of the test suspension. A neutralizer control was performed by inoculating a mixture of 9 ml of neutralizer and 1 ml of disinfectant with 100 µl of the $1:1 \times 10^5$ dilution of the titer. This produced about 360 colony forming units (CFU)/ml in the tube, which was allowed to stand for 20 minutes prior to dilution and assay by membrane filtration using duplicate 1 ml samples.

The results are provided as follows:

TABLE 13a

| | | Titer | | |
|---|---|---|---|---|
| Dilution | $1:1 \times 10^6$ | $1:1 \times 10^7$ | $1:1 \times 10^8$ | $1:1 \times 10^9$ |
| Number of Colonies | TNC* TNC | TNC TNC | 34 40 | 1 4 |

*TNC—Too Numerous to Count

TABLE 13b

| | Disinfectant solution (Example 2) | | |
|---|---|---|---|
| | Dilution of *B. anthracis* spores/disinfectant suspension | | |
| Dilution | $1:1 \times 10^1$ | $1:1 \times 10^2$ | $1:1 \times 10^3$ |
| 15 Seconds | TNC TNC | 149 99 | 6 18 |
| 30 Seconds | 4 2 | 0 0 | — — |

TABLE 13c

| Neutralization control | |
|---|---|
| Undiluted | 1:10 |
| TNC TNC | 64 61 |

Results of the titer showed a viable *B. anthracis* spore concentration of $3.70 \times 10^9$ spores per ml in the original suspension. Inoculation of 4.5 ml of disinfectant with 1.0 ml of this suspension produced an initial concentration of $3.70 \times 10^8$ spores per ml in the assay tube. Results from these procedures allowed log reduction (LR) and percent kill (PK) values to be calculated using the formulas: 1) LR=−Log(S/So) where S=concentration of viable organisms after the specified contact time, and So=the initial concentration of viable organisms at time zero; and 2) PK=(1−(S/So))×100. These values are shown below in Table 14.

TABLE 14

| | | Results | |
|---|---|---|---|
| Solution | Contact Time | Log Reduction (LR) | Percent Kill (PK) |
| Example 2 | 15 Seconds | 4.48 | 99.997 |
| Example 2 | 30 Seconds | 7.09 | 99.999992 |

Neutralization control data revealed that the neutralizer was able to adequately neutralize this disinfectant. Observed counts were greater than those expected (63 vs. 36 respectively). The disinfectant of Example 2 had relatively rapid sporicidal activity against anthrax spores. It was able to produce greater than a seven log reduction in 30 seconds, which is close to complete kill in the system employed. The disinfectant of Example 2 displayed an extremely fast kill rate on *B. anthracis* spores, compared with other common chemical disinfectants. To put this in perspective, previous data using spores from this same isolate showing that alkaline glutaraldehyde (diluted to its minimum effective concentration of 1.5%) required 50 minutes to perform a six-log reduction.

Example 13

Kill-Time Studies of Sporicidal Activity Using 2.4% Alkaline Glutaraldehyde Disinfectant A study was conducted to determine the antimicrobial activity of a 2.4% alkaline glutaraldehyde disinfectant on bacterial endospores from the test organism *Bacillus subtilis*. Glutaraldehyde disinfectant solution is a common disinfectant used in hospitals to kill bacteria and other pathogens that might otherwise be difficult to kill. This study was carried out by performing a standard kill-time suspension test using a suspension of *B. subtilis* endospores. A 15 minute contact time was evaluated.

A test suspension containing endospores from *Bacillus subtilis* (ATCC #19659) was prepared from a culture grown on Nutrient agar, to which additional sporulation enhancements were added. Plates were harvested with sterile water and endospores were purified by repeated centrifugations and resuspensions in water. The final wash was in 70 wt % ethanol for 30 minutes, to ensure the death of all vegetative bacteria. The spores were resuspended in water containing 0.1 wt % Tween 80 to prevent clumping and stored at 4° C. until used.

A neutralizer was prepared that consisted of 1 ml of freshly made, filter-sterilized sodium bisulfite solution at 5.28 wt %.

The "kill time" procedure was as follows: A 9.9 ml aliquot of the disinfectant was placed in a sterile glass culture tube. The tube was equilibrated in a 20° C. water bath. The tube of disinfectant, 9 ml of 2.4 wt % alkaline glutaraldehyde (Freshly activated CIDEXPLUS, 3.4%, Lot #:2002247TP-diluted to 2.4 wt % with sterile water), was inoculated with 100 µl of the test organism suspension at time zero. After 15 min, 1 ml of spore/disinfectant suspension was removed to 9 ml of neutralizer. The tube was mixed thoroughly. After 2 minutes, the neutralized suspension was serially diluted (1:1× 10, 1:1×10$^2$, 1:1×10$^3$, etc.) in physiological saline solution (PSS). The number of viable spores in selected dilution tubes was assayed by membrane filtration. One (1) ml aliquots were plated in duplicate. The membranes were washed with about 100 ml of sterile PSS and removed to Columbia agar plates. The plates were incubated at 37° C. for 20 hours. The number of colonies on each filter was counted and log reduction and percent kill values were computed.

As a control, a titer of the test suspension was computed by performing membrane filtration assays on selected 1:10 dilutions in PSS of the test suspension.

A neutralizer control was performed by inoculating a mixture of 1 ml of neutralizer and 1 ml of disinfectant with 100 µl of the 1:1×10$^5$ dilution of the titer. This produced about 450 CFU/ml in the tube, which was allowed to stand for 20 minutes prior to dilution and assay by membrane filtration using duplicate 1 ml samples.

The results are provided as follows:

TABLE 15a

| | Titer | | |
|---|---|---|---|
| Dilution | 1:1 × 10$^6$ | 1:1 × 10$^7$ | 1:1 × 10$^8$ |
| Number of Colonies | TNC* TNC | 96 93 | 0 0 |

*TNC—Too Numerous to Count

TABLE 15b

| Disinfectant solution (2.4 wt % alkaline glutaraldehyde disinfectant) Dilution of *B. subtilis* spores/disinfectant suspension | | | | |
|---|---|---|---|---|
| Dilution | 1:1 × 10$^1$ | 1:1 × 10$^2$ | 1:1 × 10$^3$ | 1:1 × 10$^4$ |
| 15 minutes | TNC TNC | TNC TNC | TNC TNC | 259 52 |

TABLE 15C

| Neutralization control | | |
|---|---|---|
| Dilution | 1:1 × 10$^1$ | 1:1 × 10$^2$ |
| 15 Seconds | 72 70 | 1 4 |

Sterilization controls indicated zero growth for the glutaraldehyde, sodium bisulfite, water, PSS, and Columbia agar. Results of the titer showed a viable *B. subtilis* spore concentration of 9.45×10$^8$ spores per ml in the original suspension. Inoculation of 9.9 ml of disinfectant with 100 µl of this suspension produced an initial concentration of 9.45×10$^6$ spores per ml in the assay tube. Results from these procedures allowed log reduction (LR) and percent kill (PK) values to be calculated using the formulas: 1) LR=−Log(S/So) where S=concentration of viable organisms after 1 hour, and So=the initial concentration of viable organisms at time zero; and 2) PK=(1−(S/So))×100. These values are shown below in Table 16.

TABLE 16

| Results | | | |
|---|---|---|---|
| Solution | Contact Time | Log Reduction (LR) | Percent Kill (PK) |
| Alkaline glutaraldehyde | 15 min | 0.48 | 67.1 |

Neutralization control data revealed that the neutralizer was able to adequately neutralize this disinfectant. Observed counts were greater than those expected. The 2.4 wt % alkaline glutaraldehyde solution tested had relatively slow sporicidal activity, producing only a 0.48 log-reduction in 15 minutes.

While the invention has been described with reference to certain preferred embodiments, those skilled in the art will appreciate that various modifications, changes, omissions, and substitutions can be made without departing from the spirit of the invention. It is therefore intended that the invention be limited only by the scope of the appended claims.

What is claimed is:
1. An aqueous disinfectant or sterilant composition, comprising:
 a) an aqueous vehicle, including:
  i) water;
  ii) from 0.001 wt % to 50 wt % of a peracid; and
  iii) from 0.001 wt % to 25 wt % of a peroxide, wherein the peroxide includes a peroxyhydrate,
 b) from 0.001 ppm to 50,000 ppm by weight of a colloidal transition metal or alloy thereof based on the aqueous vehicle content.
2. A composition as in claim 1, wherein the disinfectant composition is substantially free of aldehydes.

3. A composition as in claim 1, wherein the disinfectant composition is substantially free of chlorine and bromine-containing components.

4. A composition as in claim 1, wherein the disinfectant composition is substantially free of iodophore-containing components.

5. A composition as in claim 1, wherein the disinfectant composition is substantially free of phenolic-containing components.

6. A composition as in claim 1, wherein the disinfectant composition is substantially free of quaternary ammonium-containing components.

7. A composition as in claim 1, further comprising from 0.001 wt % to 95 wt % $C_1$-$C_{24}$ alcohol as part of the aqueous vehicle.

8. A composition as in claim 7, wherein $C_1$-$C_{24}$ alcohol is selected from the group consisting of methanol, ethanol, propanols, butanols, pentanols, and mixtures thereof.

9. A composition as in claim 7, wherein the $C_1$-$C_{24}$ alcohol is a polyhydric alcohol.

10. A composition as in claim 9, wherein the polyhydric alcohol includes two alcohol groups.

11. A composition as in claim 9, wherein the polyhydric alcohol includes three alcohol groups.

12. A composition as in claim 7, wherein the $C_1$-$C_{24}$ alcohol is present at from 1 wt % to 50 wt % as part of the aqueous vehicle.

13. A composition as in claim 7, wherein the $C_1$-$C_{24}$ alcohol is present at from 5 wt % to 15 wt % as part of the aqueous vehicle.

14. A composition as in claim 1, wherein the colloidal transition metal or alloy thereof is a Group VI to Group XI transition metal or an alloy thereof.

15. A composition as in claim 1, wherein the colloidal transition metal or alloy thereof is a Group X to Group XI transition metal or an alloy thereof.

16. A composition as in claim 1, wherein the colloidal transition metal or alloy thereof is selected from the group consisting of ruthenium, rhodium, osmium, iridium, palladium, platinum, copper, gold, silver, alloys thereof, and mixtures thereof.

17. A composition as in claim 1, wherein the colloidal transition metal or alloy thereof is colloidal silver.

18. A composition as in claim 1, wherein the colloidal transition metal or alloy thereof is present at from 15 ppm to 1500 ppm by weight.

19. A composition as in claim 1, wherein the peracid is an aliphatic peroxyacid.

20. A composition as in claim 1, wherein the peracid is an aromatic peroxyacid.

21. A composition as in claim 1, wherein the peracid is selected from the group consisting of peroxyformic acid, peroxyacetic acid, peroxyoxalic acid, peroxypropanoic acid, perlactic acid, peroxybutanoic acid, peroxypentanoic acid, peroxyhexanoic acid, peroxyadipic acid, peroxycitric, peroxybenzoic acid, and mixtures thereof.

22. A composition as in claim 1, wherein the peracid is present at from 0.001 wt % to 25 wt % as part of the aqueous vehicle.

23. A composition as in claim 1, wherein the peracid is present at from 1 wt % to 10 wt % as part of the aqueous vehicle.

24. A composition as in claim 1, wherein the peroxide is present at from 0.001 wt % to 10 wt % as part of the aqueous vehicle.

25. A composition as in claim 1, wherein the peroxide is present at from 1 wt % to 3 wt % as part of the aqueous vehicle.

26. A composition as in claim 1, wherein the colloidal transition metal or alloy thereof has an average particle size of from 0.001 µm to 1.0 µm.

27. A composition as in claim 1, wherein the colloidal transition metal or alloy thereof has an average particle size of from 0.030 µm to 0.5 µm.

28. A method of disinfecting a hard surface, comprising contacting the hard surface with a disinfectant composition, said composition comprising:
 a) an aqueous vehicle, including:
  i) water;
  ii) from 0.001 wt % to 50 wt % of a peracid; and
  iii) from 0.001 wt % to 25 wt % of a peroxide, wherein the peroxide is selected from the group consisting of a peroxyhydrate and a metal peroxide,
 b) from 0.001 ppm to 50,000 ppm by weight of a colloidal transition metal or alloy thereof based on the aqueous vehicle content.

29. A method as in claim 28, wherein the disinfectant composition further comprises from 0.001 wt % to 95 wt % $C_1$-$C_{24}$ alcohol as part of the aqueous vehicle.

30. A method as in claim 28, wherein $C_1$-$C_{24}$ alcohol is selected from the group consisting of methanol, ethanol, propanols, butanols, pentanols, and mixtures thereof.

31. A method as in claim 28, wherein the colloidal transition metal or alloy thereof is a Group VI to Group XI transition metal or an alloy thereof.

32. A method as in claim 28, wherein the colloidal transition metal or alloy thereof is selected from the group consisting of ruthenium, rhodium, osmium, iridium, palladium, platinum, copper, gold, silver, alloys thereof, and mixtures thereof.

33. A method as in claim 28, wherein the colloidal transition metal or alloy thereof is colloidal silver.

34. A method as in claim 28, wherein the colloidal transition metal or alloy thereof is present at from 15 ppm to 1500 ppm by weight.

35. A method as in claim 28, wherein the peracid is selected from the group consisting of peroxyformic acid, peroxyacetic acid, peroxyoxalic acid, peroxypropanoic acid, perlactic acid, peroxybutanoic acid, peroxypentanoic acid, peroxyhexanoic acid, peroxyadipic acid, peroxycitric, peroxybenzoic acid, and mixtures thereof.

36. A method as in claim 28, wherein the peracid is present at from 0.001 wt % to 25 wt % as part of the aqueous vehicle.

37. A method as in claim 28, wherein the peroxide is a metal peroxide.

38. A method as in claim 37, wherein the metal peroxide is selected from the group consisting of sodium peroxide, magnesium peroxide, calcium peroxide, barium peroxide, and strontium peroxide, and mixtures thereof.

39. A method as in claim 28, wherein the peroxide is a peroxyhydrate.

40. A method as in claim 28, wherein the peroxide is present at from 0.001 wt % to 10 wt % as part of the aqueous vehicle.

41. A method as in claim 28, wherein the disinfectant composition is substantially free of aldehydes.

42. An aqueous disinfectant or sterilant composition, comprising:

a) an aqueous vehicle, including:
   i) water;
   ii) from 0.001 wt % to 50 wt % of an peracid, said peracid including an aromatic peroxyacid; and
   iii) from 0.001 wt % to 25 wt % of a peroxide,
b) from 0.001 ppm to 50,000 ppm by weight of a colloidal transition metal or alloy thereof based on the aqueous vehicle content.

43. An aqueous disinfectant or sterilant composition, comprising:
a) an aqueous vehicle, including:
   i) water;
   ii) from 0.001 wt % to 50 wt % of a peracid; and
   iii) from 0.001 wt % to 25 wt % of a peroxide, wherein said peroxide is a metal peroxide
b) from 0.001 ppm to 50,000 ppm by weight of a colloidal transition metal or alloy thereof based on the aqueous vehicle content.

44. A composition as in claim 42, wherein the metal peroxide is selected from the group consisting of sodium peroxide, magnesium peroxide, calcium peroxide, barium peroxide, and strontium peroxide, and mixtures thereof.

45. A composition as in claim 42, wherein the disinfectant composition is substantially free of aldehydes, chlorine and bromine-containing components, iodophore-containing components, phenolic-containing components, and quaternary ammonium-containing components.

46. A composition as in claim 42, further comprising from 0.001 wt % to 95 wt % $C_1$-$C_{24}$ alcohol as part of the aqueous vehicle.

47. A composition as in claim 46, wherein $C_1$-$C_{24}$ alcohol is selected from the group consisting of methanol, ethanol, propanols, butanols, pentanols, and mixtures thereof.

48. A composition as in claim 46, wherein the $C_1$-$C_{24}$ alcohol is a polyhydric alcohol.

49. A composition as in claim 46, wherein the $C_1$-$C_{24}$ alcohol is present at from 1 wt % to 50 wt % as part of the aqueous vehicle.

50. A composition as in claim 46, wherein the $C_1$-$C_{24}$ alcohol is present at from 5 wt % to 15 wt % as part of the aqueous vehicle.

51. A composition as in claim 42, wherein the colloidal transition metal or alloy thereof is a Group VI to Group XI transition metal or an alloy thereof.

52. A composition as in claim 42, wherein the colloidal transition metal or alloy thereof is selected from the group consisting of ruthenium, rhodium, osmium, iridium, palladium, platinum, copper, gold, silver, alloys thereof, and mixtures thereof.

53. A composition as in claim 42, wherein the colloidal transition metal or alloy thereof is colloidal silver.

54. A composition as in claim 42, wherein the colloidal transition metal or alloy thereof is present at from 15 ppm to 1500 ppm by weight.

55. A composition as in claim 42, wherein the peracid is present at from 0.001 wt % to 25 wt % as part of the aqueous vehicle.

56. A composition as in claim 42, wherein the peroxide is hydrogen peroxide.

57. A composition as in claim 42, wherein the peroxide is a metal peroxide.

58. A composition as in claim 57, wherein the metal peroxide is selected from the group consisting of sodium peroxide, magnesium peroxide, calcium peroxide, barium peroxide, and strontium peroxide, and mixtures thereof.

59. A composition as in claim 42, wherein the peroxide is generated in situ.

60. A composition as in claim 59, wherein the peroxide is hydrogen peroxide generated from sodium percarbonate.

61. A composition as in claim 42, wherein the peroxide is present at from 0.001 wt % to 10 wt % as part of the aqueous vehicle.

62. A composition as in claim 42, wherein the peroxide is present at from 1 wt % to 3 wt % as part of the aqueous vehicle.

63. A composition as in claim 43, wherein the disinfectant composition is substantially free of aldehydes, chlorine and bromine-containing components, iodophore-containing components, phenolic-containing components, and quaternary ammonium-containing components.

64. A composition as in claim 43, further comprising from 0.001 wt % to 95 wt % $C_1$-$C_{24}$ alcohol as part of the aqueous vehicle.

65. A composition as in claim 64, wherein $C_1$-$C_{24}$ alcohol is selected from the group consisting of methanol, ethanol, propanols, butanols, pentanols, and mixtures thereof.

66. A composition as in claim 64, wherein the $C_1$-$C_{24}$ alcohol is a polyhydric alcohol.

67. A composition as in claim 64, wherein the $C_1$-$C_{24}$ alcohol is present at from 1 wt % to 50 wt % as part of the aqueous vehicle.

68. A composition as in claim 64, wherein the $C_1$-$C_{24}$ alcohol is present at from 5 wt % to 15 wt % as part of the aqueous vehicle.

69. A composition as in claim 43, wherein the colloidal transition metal or alloy thereof is a Group VI to Group XI transition metal or an alloy thereof.

70. A composition as in claim 43, wherein the colloidal transition metal or alloy thereof is a Group X to Group XI transition metal or an alloy thereof.

71. A composition as in claim 43, wherein the colloidal transition metal or alloy thereof is selected from the group consisting of ruthenium, rhodium, osmium, iridium, palladium, platinum, copper, gold, silver, alloys thereof, and mixtures thereof.

72. A composition as in claim 43, wherein the colloidal transition metal or alloy thereof is colloidal silver.

73. A composition as in claim 43, wherein the colloidal transition metal or alloy thereof is present at from 15 ppm to 1500 ppm by weight.

74. A composition as in claim 43, wherein the peracid is selected from the group consisting of peroxyformic acid, peroxyacetic acid, peroxyoxalic acid, peroxypropanoic acid, perlactic acid, peroxybutanoic acid, peroxypentanoic acid, peroxyhexanoic acid, peroxyadipic acid, peroxycitric, peroxybenzoic acid, and mixtures thereof.

75. A composition as in claim 43, wherein the peracid is present at from 0.001 wt % to 25 wt % as part of the aqueous vehicle.

76. A composition as in claim 43, wherein the peracid is present at from 1 wt % to 10 wt % as part of the aqueous vehicle.

77. A composition as in claim 43, wherein the peroxide is present at from 0.001 wt % to 10 wt % as part of the aqueous vehicle.

78. A composition as in claim 43, wherein the peroxide is present at from 1 wt % to 3 wt % as part of the aqueous vehicle.

* * * * *